United States Patent [19]

Criglar et al.

[11] 4,170,225
[45] Oct. 9, 1979

[54] BIOFEEDBACK DEVICE

[75] Inventors: John J. Criglar, Oakland; Lawrence T. Petraki, San Francisco, both of Calif.

[73] Assignee: Somatronics, Inc., San Francisco, Calif.

[21] Appl. No.: 777,883

[22] Filed: Mar. 16, 1977

Related U.S. Application Data

[63] Continuation-in-part of Ser. No. 724,949, Sep. 20, 1976, abandoned.

[51] Int. Cl.² ............................................. A61B 5/05
[52] U.S. Cl. .................................. 128/733; 35/22 R; 128/732
[58] Field of Search ............. 128/2.1 M, 2.1 R, 2.1 B, 128/2.1 C, 2.1 Z; 35/22 R

[56] References Cited

U.S. PATENT DOCUMENTS

| | | | |
|---|---|---|---|
| 3,548,812 | 12/1971 | Paine | 128/2.1 B |
| 3,628,538 | 12/1971 | Vincent et al. | 128/2.1 M X |
| 3,641,993 | 2/1972 | Gaarder et al. | 128/2.1 M |
| 3,730,173 | 5/1973 | Deaton | 128/2.1 Z X |
| 3,753,433 | 8/1973 | Bakerich et al. | 128/2.1 B |
| 3,905,355 | 9/1975 | Brudny | 128/2.1 M |
| 3,916,876 | 11/1975 | Freeman | 128/2.1 M |
| 3,958,563 | 5/1976 | Fernandez et al. | 128/2.1 B |
| 3,983,865 | 10/1976 | Shepard | 128/2.1 M |
| 4,014,323 | 3/1977 | Gilmer et al. | 128/2.1 Z |
| 4,031,883 | 6/1977 | Fehmi et al. | 128/2.1 B |
| 4,110,918 | 9/1978 | James et al. | 35/22 R |

OTHER PUBLICATIONS

Garland et al., "A Portable EMG Monitor", Med. Inst., vol. 8, #2, p. 127, Mar.–Apr. 1974.
Waite, "Alpha Brain Wave Feedback Monitor", Pop. Electronics, Jan. 1973, pp. 40–45.
Post, "Electromyography", Radio Electronics, Nov. 1960, pp. 34–37.

*Primary Examiner*—Lee S. Cohen
*Attorney, Agent, or Firm*—Phillips, Moore, Weissenberger, Lempio & Majestic

[57] ABSTRACT

A portable biofeedback device for monitoring electric signals produced by muscle activity is disclosed. Electrodes attached to the skin of the person being monitored couple muscle signals to a preamplifier which amplifies the signal and does preliminary filtering of unwanted frequency components in this signal. Further high and low pass filtering and amplification is then performed such that only signals in a certain frequency range are amplified. Sensitivity control is added to enable the level of detected muscle activity to be selectively set. Both visual and audio feedback is generated from the filtered and amplified signal for use by the person being monitored. The visual feedback includes easy to read visual indicators, including an overrange indicator and underrange indicator, for displaying the varying levels of muscle activity.

10 Claims, 7 Drawing Figures

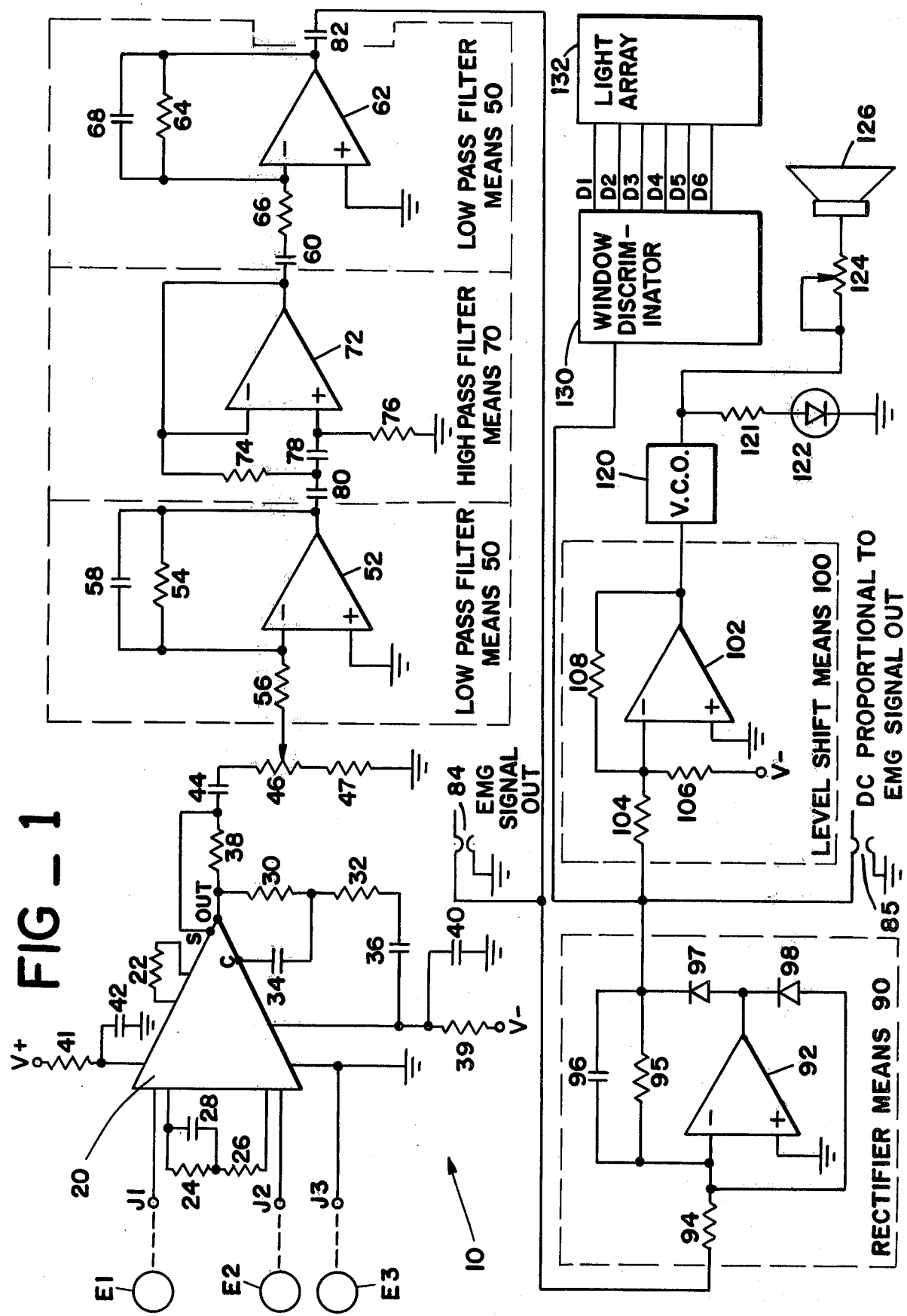

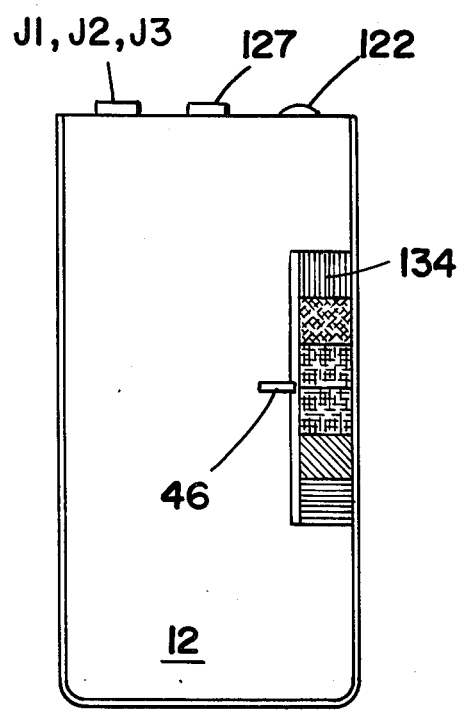
FIG _ 2
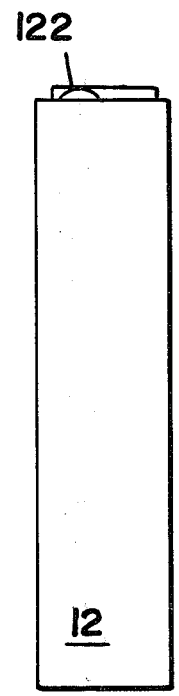
FIG _ 3
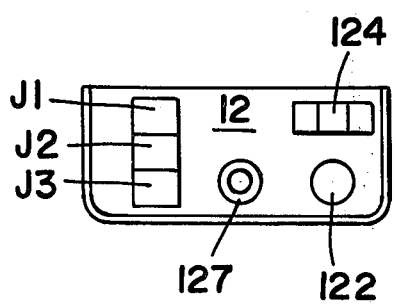
FIG _ 4
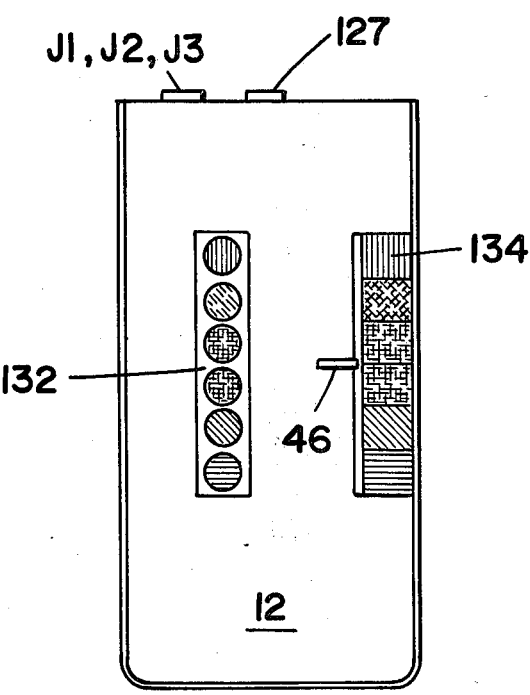
FIG _ 5

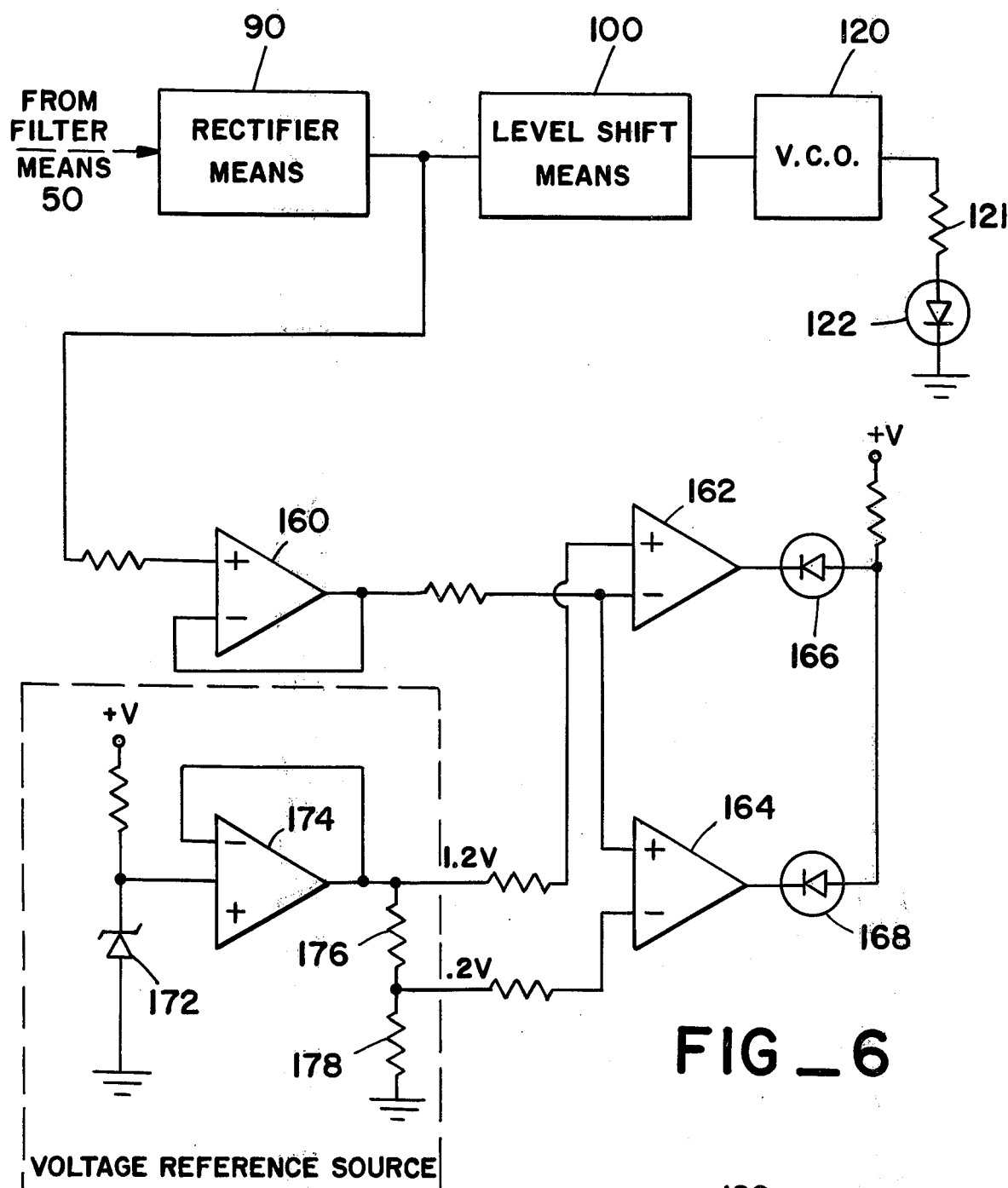
FIG_6
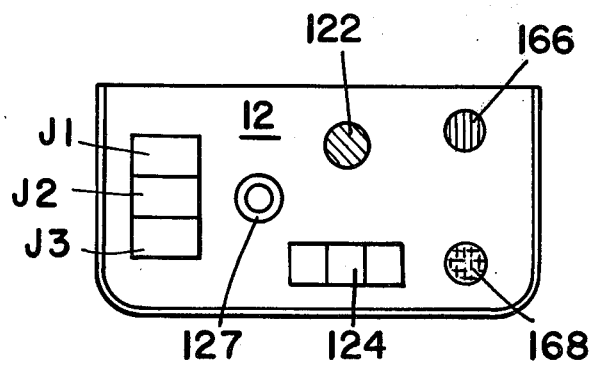
FIG_7

BIOFEEDBACK DEVICE

CROSS-REFERENCE TO RELATED APPLICATION

This is a continuation-in-part of U.S. Application Ser. No. 724,949, filed Sept. 20, 1976, now abandoned.

BACKGROUND OF THE INVENTION

In general, biofeedback devices are common in the art for monitoring brain waves, skin resistance variations, muscle activity, etc. However, most have tended to be difficult to use by untrained operators. Further, the type of feedback given has normally only either been auditory feedback or feedback by means of a meter. Thus, a small, portable device having both visual feedback and auditory feedback, and in addition including easy to use sensitivity control means is not presently available.

SUMMARY OF THE INVENTION

The present invention provides a biofeedback device for monitoring the level of muscle activity of a person. Both auditory and visual feedback is provided, with the invention contemplating using a small earphone for feedback of an audible signal, and one or more small light-emitting diodes to provide visual feedback. The audible sounds and lights would indicate, for example, the degree of hypertensive activity being experienced by a patient being monitored. The sensitivity of the biofeedback device is controlled by a sensitivity control means comprising a linear slide potentiometer including indicia such as a colored scale of rainbow hue placed alongside the potentiometer for giving an indication of the base line activity of the muscle being monitored.

Broadly stated, the invention includes means for detecting electric signals produced by muscle activity, preamplifier means for amplifying these signals, including preliminary filtering means therewith, low pass and high pass filter means including amplification of said signal therewith, sensitivity control means for enabling the level of muscle activity to be selectively set, and means for providing audio and visual feedback of the signal outputted by the low pass and high pass filter means.

Therefore, a principal object of the present invention is to provide a portable, battery operated biofeedback device for use as a training device for patients having hypertension or other muscular problems. That is, the patient can use the device as a learning tool for self-control of the level of his muscle activity. If the problem is hypertension, the device helps to reduce muscle tension, and if the problem is muscle reactivation, such as after a bone break has healed, the device helps to increase muscle activity.

A further object of the present invention is to provide a means for adjusting the sensitivity of the biofeedback device such that the user can preset the device sensitivity such that a base line is provided thereby. The user can then detect when the muscle activity exceeds a safe amount above or below this base line muscle activity level. Also, as he learns to control his own muscle activity level and consequently, to reduce or increase it, gradually he is enabled to lower or raise the base line, i.e., the sensitivity of the biofeedback device to keep the muscle signals within the monitoring range of the device.

These and other objects and advantages of the present invention will become more clear upon reference to the accompanying drawings and following description.

BRIEF DESCRIPTION OF THE DRAWINGS

FIG. 1 is an electronic schematic and partial block diagram illustrating the circuit components of the present invention;

FIG. 2 illustrates the front view of the device case of the present invention illustrating the position of various controls and indicators thereon;

FIG. 3 is a side view of the device case shown in FIG. 2;

FIG. 4 is a top view of the device case of FIG. 2;

FIG. 5 is the front view of an alternate embodiment of the device case of the present invention;

FIG. 6 is an electronic schematic illustrating the circuit components of an alternate embodiment of the visual indicia means of the present invention; and FIG. 7 is a top view of the device case of FIG. 2 illustrating the alternate visual indicia means shown in FIG. 6.

DESCRIPTION OF THE PREFERRED EMBODIMENT

The apparatus of the present invention is illustrated in the circuit schematic 10 of FIG. 1. In operation, three electrodes are attached to the skin of the person to be monitored. These electrodes detect the small amounts of charge given off by the muscles in the area of the body where the electrodes are attached. When there is increased activity or tension in these muscles, the charge given off increases. The apparatus of the present invention is designed to first amplify this signal and filter out all unwanted noise components therein, to generate a usable electromyogram (EMG) signal whose voltages is a function of the muscle activity being measured. This signal is then rectified and inputted to two devices designed to aid in the giving of useful feedback to the person being monitored as to the strength of the EMG signal detected. The two devices are a voltage controlled oscillator (VCO) whose output is coupled to a speaker, for providing audio feedback, and visual indicia means for providing visual feedback. Thus, the apparatus provides a means for indicating when muscle activity or tension has exceeded a safe level and for aiding the monitored person in reducing such tension through audio and visual feedback of the current level of muscle activity. Alternatively, the apparatus provides a means for enabling increased muscle activity to be detected and thereby reinforced, a procedure needed when muscle reactivation is desired. The ability to control changes in muscle tension in a person is what the apparatus is designed to teach, through the use of both audio and visual feedback of such tension variations.

Referring again to FIG. 1, the electrodes E1, E2 and E3, attached to the monitored person's skin, are connected to inputs J1, J2 and J3 of the present apparatus to act as a means for detecting the muscle's electrode signals. Two of the inputs J1 and J2 are fed into a preamplifier 20 and the other input J3 is used by the preamplifier 20 as a reference, or ground for the other electrode lines. The preamplifier 20 is a high input impedance, low noise instrumentation amplifier. High input impedance is required due to the extremely low strength of the signal levels sensed by the electrodes. Signals from the electrodes may have a potential on the order of $10^{-7}$ to $10^{-3}$ volts. The preamplifier 20 is needed to have low noise characteristics so that the signals generated within the amplifier circuit itself are not so large that they mask out the above-described weak signals detected by the electrodes.

The specific amplifier used herein as the preamplifier 20 is an Analog Devices AD521 amplifier. The AD521 is a newly designed low noise, high input impedance amplifier. The amplifier 20 also is a differential amplifier. That is, an output is generated by the amplifier only in response to a potential difference between inputs J1 and J2 (differential mode signal) whereas signals appearing in common on both input lines (the common mode signals) are suppressed. Also, the AD521 is an integrated circuit instrumentation amplifier that provides isolation of the input lines from the output of the amplifier. This is a major improvement over prior operational amplifiers in that in such prior devices, an external feedback resistor is required between the output and one of the inputs to the amplifier. The AD521 does not require such a connection. Thus, the fact that only differential mode signals are amplified, and the fact that the AD521 provides for high input/output isolation, allows for a high suppression of common mode signals. This feature is important in the present invention because muscle activity measurement is performed normally in a high noise environment, e.g., the electrodes act as antennas to pick up 60 cycle noise from AC power sources in the area, etc. Without any suppression of this noise, the weak signals from the electrodes would be completely masked by such noise.

The use of the AD521 amplifier also enables some filtering to be performed at this state. Filtering out unwanted frequency components is a key requirement of the current invention since only signals of a certain frequency indicate muscle activity. The range of frequencies used here is between 125 and 375 Hz. Preliminarily, note that the gain of the AD521 amplifier, as shown in FIG. 1, is determined by the ratio of the impedance of the resistor 22 to the impedance of the network comprising the resistors 24 and 26 and capacitor 28. In order to make this device insensitive to the DC potentials generated by the various electrode-electrode paste combinations (i.e., Ag-AgCl, stainless steel, etc.), the impedance of the network comprising the components 24, 26 and 28 has been selected to provide low gain for DC and low frequency signals and high gain at the desired system operating frequencies, mentioned previously, i.e., the amplifier is biased as a high pass filter. In the present embodiment, 22 is a 100 kilohm resistor, 24 is a 39 kilohm resistor, 26 is a 100 ohm resistor, and 28 is a 15 microfarad capacitor.

Some initial filtering out of high frequency components is also performed by the preamplifier 20. This high frequency roll-off above 375 Hz is provided by resistors 30 and 32 and capacitors 34 and 36. This network is tied between the output of the preamplifier 20, the compensation pin C of the preamplifier, and the negative voltage supply of the preamplifier. In the present embodiment, resistor 30 is a 680 ohm resistor, resistor 32 is 330 ohms, capacitor 34 is 0.01 microfarads, and capacitor 36 is 0.001 microfarads. Note that resistor 38, a 100 ohm resistor, is added, and a further connection between the sense pin of amplifier 20 and resistor 38 is required to protect against instability of the AD521 under certain conditions. To further isolate the preamplifier 20, filtering can also be added to the preamplifier 20's input power supplies of V+ and V−, to provide power supply isolation, i.e., to prevent any high frequency noise on these supply lines from distorting signals amplified by the preamplifier 20. Specifically, and RC circuit 39, 40, 41, 42 can be added to each supply as a low pass filter. In the present embodiment, the resistors 39, 41 are 100 ohm resistors and the capacitors 40, 42 are 15 microfarad capacitors.

The output of preamplifier 20, as modified by resistor 38, is coupled through a capacitor 44 to a sensitivity control 46 for enabling the level of detected signal activity to be selectively set. The capacitor 44 acts as an AC coupling means to ensure that only AC signals, and not DC components are transmitted to the rest of the apparatus of the present invention. The sensitivity control 46 is a variable resistor. Although a rotary potentiometer may be used, the preferred embodiment uses a linear slide resistor or potentionmeter. This resistor enables a selective amount of voltage signal provided by the preamplifier 20 to be coupled to the next stage of the present invention. Specifically, capacitor 44 is a 1.0 microfarad capacitor and resistor 46 is a 5 kilohm variable resistor. Also, a resistor 47 sets the minimum sensitivity of the system (typically 1 mv RMS at inputs J1, J2 and J3). The sensitivity control 46 enables a person being monitored to preset the device feedback sensitivity to a base line or base level. Thus, for example, as the person learns to be more relaxed at rest, due to the fact that the muscle activity feedback enables him to learn to control his muscle tension level, the sensitivity control could be adjusted to the new lower base level. Conversely, if increased muscle activity is desired, the base level can be adjusted to a new higher level as the person learns to control such muscle activity at higher and higher levels.

The present invention next provides filter means comprising both further low pass filter means 50, and secondly, further high pass filter means 70. The lower pass filter means 50, comprising two operational amplifiers, takes the signal output of said preamplifier 20 and selectively eliminates signal frequency components above a set frequency, i.e., they are rolled off and not amplified. Below this roll-off frequency, the ratio of the feedback resistor to the input resistor determines the gain of the signal. In the present embodiment, the low pass filter amplifiers are placed one on either side of the high pass filter means 70. Thus, for lower frequencies, the gain generated through amplifier 52 is the ratio of the value of resistor 54 and the value of the resistor 56. Above the frequency defined by the RC network of resistor 54 and capacitor 58, the amplification factor decreases as a function of the frequency of the signal. The output of amplifier 52 is then fed to high pass filter means 70. The output of filter means 70 is fed through another coupling capacitor 60, to further eliminate DC components in the signal, to an amplifier 62 for providing a second level of low pass filtering. Again, the ratio of the resistor 64 to the resistor 66 determines the gain generated by the amplifier 62 for the lower frequencies, and the time constant of the RC circuit comprising the resitor 64 and the capacitor 68 determines the frequency at which roll-off begins, such that the amplification of signals having frequencies higher than this decreases as a function of the frequency of such signals. The output of amplifier 62 is coupled through AC coupling capacitor 82 to rectifier means 90 described below. At this point, the signal constitutes the raw electromyogram (EMG) signal.

The output of amplifier 52, i.e., the output of the first level of low pass filtering, is coupled to the high pass filter means 70. In the filter means 70, low frequency components under 135 Hz are further selectively filtered out of the desired signal by an amplifier 72 that is biased, as is common in the art, by resistors 74 and 76 and capacitors 78 and 80. This amplifier 72 acts to fully amplify signals that are only of a frequency greater than the roll-off frequency determined by the RC circuit timing of resistors 74 and 76 and capacitors 78 and 80. Below the roll-off frequency, amplification by the amplifier 72 decreases as a function of the frequency of the signal. As mentioned above, the output of the high pass filter means 70 is coupled through AC coupling capacitor 60 to the input of amplifier 62.

The filter means signal output is rectified by means of rectifier means 90 to generate thereby a DC voltage signal proportional to said EMG signal. In the present invention, this function is performed by using an operational amplifier 92 biased in a way common in the art such that the AC input signal is converted into a DC output voltage signal that is proportional to the input signal. To do this, two diodes 97 and 98, connected as shown in FIG. 1, allow only positive going signals to be outputted by the amplifier 92. Resistors 94 and 95 are connected in the same manner as in the previously mentioned amplifiers 52, 62, etc., such that the amplifier 92 also amplifies the signal as a function of the ratio between resistor 95 to resistor 94. In the present embodiment, resistor 95 is a 10 kilohm resistor and resistor 94 is a 750 ohm resistor. Note that a capacitor 96 is also connected in parallel across resistor 95. This is to provide one last filtering stage for the signal.

In prior art devices, a raw EMG signal, or the DC voltage proportional thereto, is normally used to drive a meter or strip chart recorder. The apparatus of the present invention may include a jack 84 or 85 to allow this, to thereby provide a means for connecting such an external meter or recorder device to the present invention. However, the present apparatus is mainly designed to include means that are portable, for providing both visual and audio feedback to the person being monitored. The present invention is designed to be contained in a case, shown at 12 in FIGS. 2-5 and 7, that is approximately the size of a cigarette pack, so that it is fully portable, allowing the person being monitored to monitor himself while at work or during most other activities. Refer infra for further discussion on this aspect of the present invention.

The DC voltage signal that is outputted by the rectifier means 90 is then level shifted by level shift means 100 such that a voltage level is provided that will properly activate a voltage controlled oscillator 120. The level shifting is performed by another operational amplifier 102 biased again in a way that is common to the art. Specifically, the input to the amplifier 102 is tied to the negative voltage supply by means of a resistor 106 of 100 kilohms. Resistors 104 and 108 again are merely to provide a feedback path and an amplification factor for the amplifier 102. In the present embodiment, resistor 104 is a 20 kilohm resistor and resistor 108 is a 100 kilohm resistor.

Thus, the output of the level shift means 100 is a DC signal, whose voltage level is proportional to the input electromyogram signal, and which has been level shifted for proper operation and control of the voltage controlled oscillator 120. The voltage controlled oscillator 120 outputs a waveform whose frequency is proportional to the input DC voltage level. Such oscillators are common in the art, the present invention using a Signetics NE555V Timer for this function.

The output of the voltage controlled oscillator 120 is in a form that can be directly used to create an audible tone via a speaker 126. Note that an earphone jack 127, as seen in FIG. 4, may be provided instead of having a speaker within the case 12. A variable resistor 124 may be added to provide means for adjusting the volume of such an audible tone. A common variable resistor including on on/off switch can be used for resistor 124 to provide a simple means for turning the biofeedback device on and off.

Visual indicia means are provided to give a visual representation of the EMG signal. The output of the VCO 120 may be connected through resistor 121 to a light source, such as light emitting diode (LED) 122, which flashes at a rate proportional to the control voltage present at the output of level shift means 100. As the EMG activity varies, the visual flashing rate and the audio rate proportionally vary. It should be noted that the VCO 120 exhibits a "window" such that when the control voltage into the VCO falls within this window, the operating frequency varies along with the control voltage. When the control voltage is above the window level, the VCO frequency remains fixed at the maximum frequency and when the control voltage lies below this window level, the VCO remains at its lowest frequency. This "training window", along with the use of a linear slide potentiometer sensitivity control 46 are some of the unique features of this device which allows an untrained user to set the training window to his own muscle activity level without needing trained operators to set up the equipment for his biofeedback session.

An alternate visual indicia means would be to couple the rectifier 90 output to a window discriminator 130. This discriminator 130 operates to turn on one or more of a plurality of output lines, e.g., output lines D1-D6, as a function of the amplitude of the signal being inputted to the discriminator 130. Note that a window discriminator operating as a function of input frequency could similarly be coupled to the VCO 120 output to provide the same functioning as the discriminator 130. As can be seen, if each of the discriminator 130 output lines D1-D6 are tied to a light array 132, a visual indicia means, the person being monitored can see from the array 132 what his present EMG level is. The simplest light array 132 would be to have a single light tied to each of the output lines D1-D6 of the discriminator 120. Such lights could be colored such that the lowest level of EMG activity would light a blue light. Lights indicating higher levels of activity would have different colors with the highest level activity light, connected to output D6, being a red color.

A second alternate visual indicia means is illustrated in FIG. 6. This embodiment is designed to assist the device user in setting his "training window", that is, setting the gain of the device such that the signal being received by the biofeedback device is within the operating range of the device. Specifically, two lights are added to act as range limits. One light goes on when the rectified EMG signal exceeds the upper range of the device, i.e., it provides a means for indicating an overrange signal. The other added light goes on when the rectified EMG falls below a set level, i.e., it provides a means for indicating an underrange signal. The overrange voltage level and underrange voltage level are set near the points where the VCO 120 has its maximum and minimum operating frequencies. In the present embodiment, the overrange voltage level is set at 1.2 volts DC and the underrange voltage level is set at 0.25 volts DC. Consequently, when the user sets the gain control to a point where neither of the two lights are on, he knows he is within the device 10 operating range. Note that the overrange and underrange lights may also be used as presetable user "goals" for relaxation or muscle re-education training, to consequently, constitute a form of binary feedback information. Note also that, in this embodiment, it is envisioned that only the one LED light 122 would be providing visual feedback to the device user when the device 10 is detecting an EMG signal presently within the operating range of the device 10.

Referring now to FIG. 6, shown is a circuit for providing the means for detecting the overranging and underranging of the EMG signal. The EMG signal, as rectified by rectifier means 90 is coupled through a buffer amplifier 160 in a conventional manner, and the output of this amplifier 160 is coupled to two comparators 162 and 164. The signal coupled to comparator 162 is coupled to the negative of this comparator 162. However, it is connected to the positive input of the other comparator 164. The output of comparator 162 drives an LED light 166 identified as the overrange light. Similarly, the output of comparator 164 drives an LED light 168 identified as the underrange light. The reason the EMG input signal to the two comparators 162,164 is coupled to different polarity inputs of these comparators is that one comparator, comparator 164 is designed to be on until a certain minimum voltage level is surpassed, whereas comparator 162 is designed to be off until a certain voltage level is detected, the maximum operating range voltage level. The voltage levels at which the two comparators 162 and 164 are caused to change state, are generated by voltage reference source 170. In the present embodiment, the voltage reference source 170 generates a 0.25 volt and a 1.2 volt output which are used respectively to cause comparator 164 to change state at 0.25 volts and cause the comparator 162 to change state at 1.2 volts. The voltage reference source 170 is conventional, with a zener diode 172 acting to generate the required stable voltage level for a amplifier 174. The output of this amplifier 174 is fed into a resistor network comprising resistors 176 and 178 which provide a means for conventionally generating two voltages out of the initial 1.2 voltage level.

As was mentioned above, a variable resistor 46 is provided as part of the present invention to act as sensitivity control means for the EMG signal being detected. With this control device, when one initially starts monitoring himself with the present invention he would set the sensitivity such that the audio and visual output would respond to one level of muscle activity or tension level. As the person being monitored begins to improve by learning to control the level of tension in his muscles, the sensitivity means 46 allows that person to vary the feedback sensitivity displayed, so that, if tension reduction was being learned, the circuit thereby becomes more sensitive to input signals. That is, a smaller signal would now cause red light 166, for example, to indicate an overrange condition. Similarly, a smaller signal would be within the device operating range. Thus, using the present invention one can continue to train oneself to further decrease or increase the level of muscle activity being monitored without going outside of the sensitivity range of the present invention.

FIG. 2 illustrates the front view of the case of the present invention illustrating one embodiment of controls and indicators arranged thereon. As is seen, the slide potentiometer 46 has juxtaposed to it an indicator means 134 such that a visual indication of the base level or feedback sensitivity of the device is provided. The indicator means 134 may comprise a multicolored scale defining a low end beginning with a blue color to a high end having a red color with a range of coloration therebetween. The blue color end indicates where the sensitivity is highest, i.e., if one can set his base level here, his muscle activity is very low.

The indicator means 134 may also comprise a scale indicator with markings dividing up the sensitivity control travel into ruled segments, e.g. segments 1–10. With such a scaled indicator, the precise sensitivity may, for example, be preset or reset to coincide with a previous known sensitivity level.

Note that an earphone jack 127 is shown as part of the speaker means, with an earphone, not shown, used to generate the audible tones. Also, the visual indicia means shown in FIG. 2 is an LED 122.

FIG. 5 illustrates the first alternate embodiment for the visual indicia means of FIG. 2. Shown is a light array 132 in the form of a plurality of serially positioned lights. Similar to the indicator means 134, these lights are in a range of colors with the red light at the top indicating high muscle activity within a given sensitivity range, and with the blue light at the bottom indicating low muscle activity.

FIG. 7 illustrates the second alternate embodiment for the visual indicia means as disclosed in FIG. 6. Shown are three light-emitting diodes, LED's 122, 166 and 168. LED 122 again is used for providing biofeedback of the detected EMG signal when this signal is set by the sensitivity control 46 to be within the operating range of the device 10. The red overrange light is shown at 166, as described above. It goes on when the rectified EMG signal detected by the device 10 exceeds 1.2 volts DC. The other level indicating light, the yellow underrange light, is shown at 168, as described above. This light only goes on when the rectified EMG signal detected by the device is below 0.25 volts. As seen in FIG. 7, the layout of the rest of the components on the top of the device 10 remain in locations similar to the locations shown in FIG. 4.

It is to be understood that the foregoing description is merely illustrative of preferred embodiments of the invention and that the scope of the invention is not to be limited thereto, but is to be determined by the scope of the appended claims.

What is claimed is:

1. A biofeedback device for monitoring the electric signal produced by muscle activity or the like including means for detecting and amplifying said electric signal, filter means for suppressing unwanted components of said detected signal, sensitivity control means for enabling the level of said detected signal to be selectively set, and means for providing visual feedback of the signal output by said filter means, said visual feedback means comprising:

rectifier means for generating a D.C. voltage signal proportional to said signal output by said filter means; and visual indicia means for providing a visual output representative of said D.C. voltage signal, and including a light array in the form of a plurality of serially positioned lights.

2. The apparatus of claim 1, wherein said visual indicia means further comprises a window discriminator operatively connected between said rectifier means and said light array and functioning to turn on said lights such that as said detected signals increase in amplitude, more and more lights are caused to turn on.

3. The apparatus of claim 2 wherein said lights are in a range of colors.

4. The apparatus of claim 2 wherein said visual indicia means further comprises:
   level shift means for shifting the voltage level of said D.C. voltage signal;
   voltage controlled oscillator means for generating an output frequency in the audio range proportional to said level shifted D.C. voltage signal; and
   a light source operatively connected to said voltage controlled oscillator means for providing a visual output as a function thereof.

5. A biofeedback device for monitoring the electrical signal produced by muscle activity or the like including means for detecting and amplifying said electric signal, filter means for suppressing unwanted components of said detected signal, sensitivity control means for enabling the level of said detected signal to be selectively set, and means for providing visual feedback of the signal output by said filter means, said visual feedback means comprising:
   rectifier means for generating a D.C. voltage signal proportional to said signal output by said filter means; and
   visual indicia means for providing a visual output representative of said D.C. voltage signal, and including:
   oscillator means for generating an output frequency proportional to said D.C. voltage signal;
   a light source operatively connected to said oscillator means for providing a visual output as a function thereof;
   means for detecting a voltage overrange in said D.C. voltage signal;
   means for detecting a voltage underrange in said D.C. voltage signal;
   overrange indicator means for visually indicating said detected voltage overrange; and
   underrange indicator means for visually indicating said detected voltage underrange.

6. The apparatus of claim 5 wherein said sensitivity control means comprises a variable potentiometer juxtaposed to indicator means whereby the position of said variable potentiometer relative to said indicator means gives a visual indication of feedback sensitivity.

7. The apparatus of claim 6 wherein said variable potentiometer comprises a linear travel slide potentiometer.

8. The apparatus of claim 5 wherein said means for detecting a voltage overrange in said DC voltage signal comprises:
   first comparator means; and
   means for generating a first preset voltage reference corresponding to the desired voltage overrange level and for coupling said first voltage reference to said first comparator means, said first comparator means acting in response thereto to change state when the voltage level of said DC voltage signal exceeds said first voltage reference.

9. The apparatus of claim 8 wherein said means for detecting a voltage underrange in said DC voltage signal comprises:
   second comparator means; and
   means for generating a second preset voltage reference corresponding to the desired voltage underrange level and for coupling said second voltage reference to said second comparator means, said second comparator means acting in response thereto to change state when the voltage level of said DC voltage signal falls below said second voltage reference.

10. The apparatus of claim 5 further comprising:
    speaker means operatively connected to said oscillator means, for outputting an audible tone as a function thereof.

* * * * *